(12) United States Patent
Pernot et al.

(10) Patent No.: US 12,138,111 B2
(45) Date of Patent: Nov. 12, 2024

(54) METHOD FOR MEASURING THE SPEED OF SOUND IN LIVER WITH A SPECIFIC PROBE AND ASSOCIATED METHODS AND DEVICES

(71) Applicants: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); UNIVERSITÉ PARIS CITÉ, Paris (FR); SORBONNE UNIVERSITÉ, Paris (FR); ECOLE SUPERIEURE DE PHYSIQUE ET DE CHIMIE INDUSTRIELLES DE LA VILLE DE PARIS, Paris (FR)

(72) Inventors: Mathieu Pernot, Paris (FR); Thomas Deffieux, Paris (FR); Mickael Tanter, Paris (FR); Clément Papadacci, Paris (FR)

(73) Assignees: INSTITUT NATIONAL DE LA SANTE ET DE LA RECHERCHE MEDICALE (INSERM), Paris (FR); CENTRE NATIONAL DE LA RECHERCHE SCIENTIFIQUE—CNRS, Paris (FR); UNIVERSITÉ PARIS CITÉ, Paris (FR); SORBONNE UNIVERSITÉ, Paris (FR); ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 0 days.

(21) Appl. No.: 17/763,259

(22) PCT Filed: Sep. 25, 2020

(86) PCT No.: PCT/EP2020/076886
§ 371 (c)(1),
(2) Date: Mar. 24, 2022

(87) PCT Pub. No.: WO2021/058731
PCT Pub. Date: Apr. 1, 2021

(65) Prior Publication Data
US 2022/0346749 A1 Nov. 3, 2022

(30) Foreign Application Priority Data
Sep. 25, 2019 (EP) .................................. 19306198

(51) Int. Cl.
*A61B 8/08* (2006.01)
*A61B 8/00* (2006.01)
(Continued)

(52) U.S. Cl.
CPC ............ *A61B 8/0858* (2013.01); *A61B 8/085* (2013.01); *A61B 8/4494* (2013.01); *A61B 8/485* (2013.01);
(Continued)

(58) Field of Classification Search
CPC ..... A61B 8/0858; A61B 8/085; A61B 8/4494; A61B 8/485; A61B 8/5223; A61B 8/54;
(Continued)

(56) References Cited

U.S. PATENT DOCUMENTS 10,107,645 B2 * 10/2018 Hajati .................... G01N 29/34
2009/0003128 A1 1/2009 Jeong et al.
(Continued)

OTHER PUBLICATIONS

Marion Imbault et al. "Robust sound peed estimation for ultrasound-based hepatic steatosis assessment", Physics in Medicine and Biology, Institute of Physics Publishing Bristol GB, vol. 62, No. 9, Apr. 5, 2017 (Apr. 5, 2017), pp. 3582-3598 (Year: 2017).*
(Continued)

*Primary Examiner* — Baisakhi Roy
*Assistant Examiner* — Kaitlyn E Sebastian
(74) *Attorney, Agent, or Firm* — WC&F IP

(57) ABSTRACT

Because of the increase of the obesity related diseases, it is desirable to be able to detect a fatty liver and quantify the content in fat for the fatty liver. Known methods are biopsy and magnetic resonance imaging. However, biopsy is an invasive method and magnetic resonance imaging is a complicated method to carry out. The inventors propose a new ultrasonic method, which is more compliant with a
(Continued)

regular control of the content in fat for the fatty liver for a subject. This method notably relies on a smart exploitation of the coherence properties of ultrasound pulses applied to the liver. This method has already been validated on sane subjects as providing accurate measurements, notably for fat content.

14 Claims, 7 Drawing Sheets

(51) Int. Cl.
*G01S 7/52* (2006.01)
*G01S 15/89* (2006.01)
*G16H 50/30* (2018.01)

(52) U.S. Cl.
CPC .............. *A61B 8/5223* (2013.01); *A61B 8/54* (2013.01); *G01S 7/52049* (2013.01); *G01S 15/8922* (2013.01); *G16H 50/30* (2018.01)

(58) Field of Classification Search
CPC ..... A61B 8/4254; A61B 8/14; G01S 7/52049; G01S 15/8922; G01S 15/8925; G16H 50/30; G01N 29/4418; G01N 2291/02475; G01N 2291/044; G01N 29/07; G01H 5/00
See application file for complete search history.

(56) References Cited

U.S. PATENT DOCUMENTS

| | | | | |
|---|---|---|---|---|
| 2009/0270735 | A1* | 10/2009 | Cerofolini | B06B 1/0637 600/459 |
| 2013/0218012 | A1* | 8/2013 | Specht | G01S 15/8929 367/7 |
| 2017/0258448 | A1* | 9/2017 | Maruyama | G01S 15/8929 |

OTHER PUBLICATIONS

Hideki Kumagai et al. "A New Method for Measuring the Speed of Sound in Rat Liver ex Vivo using an Ultrasound system: Correlation of Sound Speed with Fat Deposition", Ultrasound in Medicine and Biology., vol. 40, No. 10, Oct. 1, 2014 (Oct. 1, 2014), pp. 2499-2507 (Year: 2014).*

UnitConverters.net (2008). http://www.unitconverters.net/frequency-wavelength/megahertz-to-wavelength-in-millimetres.htm. (Year: 2008).*

Imbault et al.; "Robust sound speed estimation for ultrasound-based hepatic steatosis assessment"; Physics in Medicine and Biology, vol. 62, No. 9, Apr. 5, 2017, pp. 3582-3598.

Kumagai et al.; "A New Method for Measuring the Speed of Sound in Rat Liver ex Vivo Using an Ultrasound System: Correlation of Sound Speed with Fat Deposition"; Ultrasound in Medicine and Biology, vol. 40, No. 10, Oct. 1, 2014, pp. 2499-2507.

Hasegawa et al.; "Initial phantom study on estimation of speed of sound in medium using coherence among received echo signals"; Jounal of Medical Ultrasonics, vol. 46, No. 3, Mar. 8, 2019, pp. 297-307.

Imbault et al.; "Ultrasonic fat fraction quantification using adaptive sound speed estimation"; Physics in Medicine and Biology, vol. 63, No. 21, Oct. 26, 2018, p. 215013.

* cited by examiner

METHOD FOR MEASURING THE SPEED OF SOUND IN LIVER WITH A SPECIFIC PROBE AND ASSOCIATED METHODS AND DEVICES

TECHNICAL FIELD OF THE INVENTION

The present invention concerns a method for measuring at least one parameter of in a region of interest of an organ among which the speed of sound. The invention is also relative to a method for post-processing images of a region of interest of an organ of a subject. The invention concerns a method for predicting that a subject is at risk of suffering from an obesity related disease. The invention also relates to a method for diagnosing an obesity related disease. The invention also concerns a method for identifying a therapeutic target for preventing and/or treating an obesity related disease. The invention also relates to a method for identifying a biomarker, the biomarker being a diagnostic biomarker of an obesity related disease, a prognostic biomarker of an obesity related disease or a predictive biomarker in response to the treatment of an obesity related disease. The invention also concerns a method for screening a compound useful as a medicine, the compound having an effect on a known therapeutical target, for preventing and/or treating an obesity related disease. The invention also relates to the associated computer program product and computer readable medium. The present invention also concerns a device for measuring.

BACKGROUND OF THE INVENTION

Liver diseases are drastically increasing in developed countries and are responsible for more than 250,000 deaths per year in Europe as evaluated in 2012. Liver diseases belong to the obesity related diseases. The obesity related diseases encompass the cancer, the type 2 diabetes, heart disease, non-alcoholic fatty liver disease (NAFLD) and nonalcoholic steatohepatitis (NASH) which is the most severe form of NAFLD.

Obesity related diseases are notably associated with liver steatosis a degeneration of fatty liver condition which is an abnormal accumulation of fat in liver cells. Fatty liver is a reversible condition and its early detection could prevent the development of steatosis.

Because of the increase of the obesity related diseases, it is desirable to be able to detect a fatty liver and quantify the content in fat for this fatty liver.

Liver biopsy is a method that is used to evaluate the percentage of liver fat in clinics.

However, biopsy can only be performed on extremely small samples. Such small sizes result in certain cases in an impossibility to provide with a definitive diagnosis because of the lack of information.

In addition, biopsy is a very invasive technique which is very traumatic for the organism.

It should also be noted that biopsy implies an histologic evaluation which is subjective and depends on the experience of the pathologist.

Furthermore, one difficulty is the fact that biopsy is generally only suggested for patients which are already suffering from steatosis. This is not in line with the detection of a fatty liver at an early stage wherein the subjects are asymptomatic.

Therefore, biopsy cannot be used as a simple routine exam for detection or follow-up of fatty liver condition.

To remediate these disadvantages of the biopsy, magnetic resonance imaging (MRI) is an imaging technique that is non-invasive.

One method is to use images obtained by MRI for estimating the proton-density fat fraction (PDFF) as a measure of fractional fat content.

However, MRI suffers several limitations such as cost, contra-indications and poor availability.

As a consequence, using MRI for controlling regularly fatty liver condition is reserved for a few people.

It is also known an article by Marion Imbault et al. whose title is "Robust sound speed estimation for ultrasound-based hepatic steatosis assessment" and which was published in the review Physics in Medicine and Biology, volume 62, number 9 of Apr. 5, 2017.

As explained in the abstract of this article, the main objectives of the study, which leads to the article, are to propose a robust method for sound speed estimation (SSE) locally in the liver and to assess its accuracy for steatosis detection and imaging. This technique was first validated on two phantoms and SSE was assessed with a precision of 0.006 and 0.003 mm.µs−1 respectively the two phantoms. Then a preliminary clinical trial (N=17 patients) was performed. SSE results was found to be highly correlated with MRI proton density fat fraction ($R^2$=0.69) and biopsy (AU-ROC=0.952) results. This new method based on the assessment of spatio-temporal properties of the local speckle noise for SSE provides an efficient way to diagnose and stage hepatic steatosis. Another article from Hideki KUMAGAI et al. is known. It is entitled "A new method for measuring the speed of sound in rat liver ex vivo using an ultrasound system: correlation of sound speed with fat deposition" and was published in the review Ultrasound in Medicine and Biology, volume 40, number 10 of Oct. 1, 2014.

According to the authors of this article, they were able to achieve a new non-invasive method that would be clinically applicable for measurement of sound speed in the liver. Sprague-Dawley rats were divided into two groups: a control group and a fatty liver group prepared by keeping the rats on a choline-deficient diet for 6 weeks. The livers were subjected to pathologic and biochemical analysis; the speed of sound through the liver tissue was measured using their proposed method and a pulser-receiver as standard. Their results indicated that using their proposed method makes it feasible to diagnose fatty liver with good accuracy on the basis of sound speed.

The article by Hasagawa HIDEYUKI et al. whose title is "Initial phantom study on estimation of speed of sound in medium using coherence among received echo signals" is another article that can be found in the prior art. This article was published in the review Journal of Medical Ultrasonics (volume 46, number 3) in 2019.

In this article, it is noted that ultrasound beamforming is required to obtain clinical ultrasound images. In the beamforming procedure, the distance between the receiving focal point and each transducer element is determined based on the assumed speed of sound in the tissue. However, the actual speed of sound in tissue is unknown and varies depending on the tissue type. To improve the performance of an ultrasonic beamformer by evaluating its focusing quality, the coherence factor (CF) was introduced in medical ultrasound imaging. The CF may be used to estimate the speed of sound in tissue because it can identify focusing errors in beamforming. In the present study, the feasibility of CF for estimating the speed of sound was examined through phantom experiments. It is shown that the speed of sound of a homogeneous medium could be determined by the proposed method with errors of less than 1% using CFs obtained from ultrasonic echo signals selected based on the CF-weighted echo amplitudes, i.e., when echo signals with better signal-to-noise ratios (SNRs) were used.

SUMMARY OF THE INVENTION

There is therefore a need for a method which can be used for detecting a fatty liver and quantifying the content in fat for this fatty liver and which is easier to implement.

To the end, the specification also concerns a method for measuring at least one parameter of a region of interest of an organ of a subject, the organ being preferably the liver, one parameter being the global speed of sound in the region of interest, the global speed of sound in the region of interest being the integration of the speed of sound at several depths of the region of interest, the speed of sound at a given depth being named a local speed of sound, the method comprising a step of obtaining over time several backscattered echoes from the region of interest corresponding to several excitations of the region of interest by ultrasound pulses applied with an ultrasound probe, the ultrasound probe comprising elements of transducer, a step of choosing an assumed value for the speed of sound to be measured and a step of calculating correlation coefficients of at least one backscattered echoes by using the assumed value, a correlation coefficient being equal to the correlation between the echo signal backscattered by a region of the tissue and received by a first element of transducer and the echo backscattered by the same region and received by a second element of transducer positioned at a given distance from the first element of transducer, the correlation coefficients being calculated for several pairs of elements of transducer corresponding to several distances. The method for measuring further comprises a step of iterating the choosing step and the calculating step for several assumed values for the speed of sound to be measured and a step of determining the global speed of sound to be measured based on applying an optimization criteria on the calculated correlation coefficients obtained for each assumed values for the speed of sound to be measured. In such case, the ultrasound probe comprises a set of elements of transducers arranged according to a spatial arrangement in which at least some of the elements of transducers are arranged along circles.

Such method can be formulated in an other way which is a use of a ultrasound probe comprising a set of elements of transducers arranged according to a spatial arrangement in which at least some of the elements of transducers are arranged along circles, the use being a use for a method for measuring at least one parameter of a region of interest of an organ of a subject, the organ being preferably the liver, one parameter being the global speed of sound in the region of interest, the global speed of sound in the region of interest being the integration of the speed of sound at several depths of the region of interest, the speed of sound at a given depth being named a local speed of sound, the method comprising a step of obtaining over time several backscattered echoes from the region of interest corresponding to several excitations of the region of interest by ultrasound pulses applied with an ultrasound probe, the ultrasound probe comprising elements of transducer, a step of choosing an assumed value for the speed of sound to be measured and a step of calculating correlation coefficients of at least one backscattered echoes by using the assumed value, a correlation coefficient being equal to the correlation between the echo signal backscattered by a region of the tissue and received by a first element of transducer and the echo backscattered by the same region and received by a second element of transducer positioned at a given distance from the first element of transducer, the correlation coefficients being calculated for several pairs of elements of transducer corresponding to several distances. The method for measuring further comprises a step of iterating the choosing step and the calculating step for several assumed values for the speed of sound to be measured and a step of determining the global speed of sound to be measured based on applying an optimization criteria on the calculated correlation coefficients obtained for each assumed values for the speed of sound to be measured.

Thanks to the invention, a non-invasive method which is easily developable for each person in the world is proposed. This method can be used for detecting a fatty liver and quantifying the content in fat for this fatty liver.

It is to be noted that the proposed method enables to obtain a better accuracy in the speed of sound with the help of a very specific ultrasound probe. This specific ultrasound probe is very different from the usual ultrasound probes, which are linear transducer or array transducer.

This means the present invention is compatible with a simple ultrasound probe, which is counterintuitive since the person skilled in the art thinks that obtaining a coherence measurement necessitates an ultrasound with a large spatial scope and an improved post-processing. Indeed, the person skilled in the art would have searched for improved optimization criteria.

According to further aspects which are advantageous but not compulsory, this use might incorporate one or several of the following features, taken in any technically admissible combination:
  the circles are concentric.
  the ultrasound probe comprises less than 5 circles.
  elements of transducer of the ultrasound probe are arranged along additional portions of circles.
  the additional portions of circles are symmetrical.
  the additional portions are linked with the largest circles.
  an operating wavelength is defined for the ultrasound probe, the space between two circles being inferior or equal five times the operating wavelength.
  the ultrasound probe comprises a set of transducer elements and the number of transducer elements is comprised between 3 and 64.
  the optimization criteria is maximizing at least one of the autocorrelation function and the coherence factor, the coherence factor being proportional to the ratio of the coherent ultrasound energy received by the ultrasound probe and the incoherent ultrasound energy received by the ultrasound probe
  the method comprises carrying out one of the following calculation technique: a first calculation technique in which a spatial coherence function corresponding to the evolution of the value of the correlation coefficients with distance for each backscattered echoes is established, and a statistical estimator is applied to the established spatial coherence functions to obtain a mean spatial coherence function, and a second calculation technique in which a statistical estimator is applied to the correlation coefficients calculated at the same distance for several received backscattered echoes to obtain mean correlation coefficients.
  the organ comprises a tissue structure, the propagation of sound in the tissue structure with depth being modeled by a layered model comprising several layers with depth, the method for measuring further comprising deducing several local speeds of sound of the region of interest from several global speeds of sound by using the layered model, the global speeds of sound being measured for respective depths, said depths comprising at least one depth per layer of the layered model.

The specification also proposes a method for measuring at least one parameter of a region of interest of an organ of a subject, one parameter being the global speed of sound in the region of interest, the global speed of sound in the region of interest being the integration of the speed of sound at several depths of the region of interest, the speed of sound at a given depth being named a local speed of sound, the method comprising a step of obtaining over time several backscattered echoes from the region of interest corresponding to several excitations of the region of interest by ultrasound pulses applied with an ultrasound probe, the ultrasound probe comprising elements of transducer, a step of choosing an assumed value for the speed of sound to be measured and a step of calculating correlation coefficients of at least one backscattered echoes by using the assumed value, a correlation coefficient being equal to the correlation between the echo signal backscattered by a region of the tissue and received by a first element of transducer and the echo backscattered by the same region and received by a second element of transducer positioned at a given distance from the first element of transducer, the correlation coefficients being calculated for several pairs of elements of transducer corresponding to several distances. The method for measuring further comprises a step of iterating the choosing step and the calculating step for several assumed values for the speed of sound to be measured and a step of determining the global speed of sound to be measured based on applying an optimization criteria on the calculated correlation coefficients obtained for each assumed values for the speed of sound to be measured. The ultrasound probe and the region of interest are moved relatively to each other between each excitation.

According to further aspects which are advantageous but not compulsory, the method for measuring might incorporate one or several of the following features, taken in any technically admissible combination:

- the organ being the liver.
- the optimization criteria is maximizing at least one of the autocorrelation function and the coherence factor, the coherence factor being proportional to the ratio of the coherent ultrasound energy received by the ultrasound probe and the incoherent ultrasound energy received by the ultrasound probe.
- the method comprises carrying out one of the following calculation technique: a first calculation technique in which a spatial coherence function corresponding to the evolution of the value of the correlation coefficients with distance for each backscattered echoes is established, and a statistical estimator is applied to the established spatial coherence functions to obtain a mean spatial coherence function, and a second calculation technique in which a statistical estimator is applied to the correlation coefficients calculated at the same distance for several received backscattered echoes to obtain mean correlation coefficients.
- the organ comprises a tissue structure, the propagation of sound in the tissue with depth being modeled by a layered model comprising several layers with depth, the method for measuring further comprising deducing several local speeds of sound of the region of interest from several global speeds of sound by using the layered model, the global speeds of sound being measured for respective depths, said depths comprising at least one depth per layer of the layered model.
- the region of interest is the liver and at least one layer of the layered model comprises the skin situated between the liver and the ultrasound probe.
- the method comprises a step of measuring the value of the relative movement between the ultrasound probe and the region of interest, the step of measuring being carried out by using an accelerometer.
- the obtaining step is automatically triggered by a sensor that detects the motion of the ultrasound probe.
- the measurements are automatically triggered by a sensor that detects the motion of the probe.
- the method comprises a step of displaying data concerning the relative movement between two successive excitations, the data preferably comprising data relative to the fulfilment of one the following requirements: a minimum amplitude is strictly superior to an operating ultrasound wavelength defined for the ultrasound probe, the minimum amplitude being defined for the relative movement between two successive excitations, a maximum amplitude is strictly inferior to 20 millimeters, a maximum amplitude is defined for the relative movement between two successive excitations, and the relative movement between two successive excitations corresponds to an area having a surface superior to 10 $mm^2$.
- the number of excitations within the area is superior to 10.
- the transducer elements presents one of the following properties the number of transducer elements is comprised between 3 and 64, and the transducer elements are arranged along concentric circles.
- the relative movement between two successive excitations is carried out along predefined lines, notably circles.
- the method further comprises obtaining at least one additional parameter of the region of interest by carrying out one of the following steps: a step of measuring at least another physical value which is chosen in the group consisting of a value representative of shear velocity or stiffness, a value representative of deformation, the shear viscosity, the contractility, the degree of anisotropy of the fibers comprised in the region of interest and the direction of the fibers comprised in the region of interest, each measured physical value being an additional parameter, and a step of determining the fat content of the region of interest based on the deduced speed of sound, the determined fat content being an additional parameter.

The specification further describes a method for post-processing images of a region of interest of an organ of a subject to obtain determined parameters, the organ being preferably the liver, one parameter being the global speed of sound in the region of interest, the global speed of sound in the region of interest being the integration of the speed of sound at several depths of the region of interest, the speed of sound at a given depth being named a local speed of sound, the images being acquired by obtaining over time several backscattered echoes from the region of interest corresponding to several excitations of the region of interest by ultrasound pulses applied with an ultrasound probe, the ultrasound probe comprising elements of transducer, the ultrasound probe and the region of interest being moved relatively to each other between each excitation, the method for post-processing comprising at least a step of choosing an assumed value for the speed of sound to be measured, a step of calculating correlation coefficients of at least one backscattered echoes by using the assumed value, a correlation coefficient being equal to correlation between the echo signal backscattered by a region of the tissue and received by a first element of transducer and the echo backscattered by the same region and received by a second element of transducer positioned at a given distance from the first element of transducer, the correlation coefficients being calculated for several pairs of elements of transducer corresponding to several distances, a step of iterating the choosing step and the calculating step for several assumed values for the speed of sound to be measured, and a step of determining the global speed of sound to be measured based on applying an optimization criteria on the calculated correlation coefficients obtained for each assumed values for the speed of sound to be measured.

Alternatively, the present specification describes a method for post-processing images of a region of interest of an organ of a subject to obtain determined parameters, the organ being preferably the liver, one parameter being the global speed of sound in the region of interest, the global speed of sound in the region of interest being the integration of the speed of sound at several depths of the region of interest, the speed of sound at a given depth being named a local speed of sound, the images being acquired by obtaining over time several backscattered echoes from the region of interest corresponding to several excitations of the region of interest by ultrasound pulses applied with an ultrasound probe, the ultrasound probe comprising elements of transducer. The method for post-processing comprising at least a step of choosing an assumed value for the speed of sound to be measured, a step of calculating correlation coefficients of at least one backscattered echoes by using the assumed value, a correlation coefficient being equal to the correlation between the echo signal backscattered by a region of the tissue and received by a first element of transducer and the echo backscattered by the same region and received by a second element of transducer positioned at a given distance from the first element of transducer, the correlation coefficients being calculated for several pairs of elements of transducer corresponding to several distances. The method further comprises a step of iterating the choosing step and the calculating step for several assumed values for the speed of sound to be measured, and a step of determining the global speed of sound to be measured based on applying an optimization criteria on the calculated correlation coefficients obtained for each assumed values for the speed of sound to be measured. The ultrasound probe is arranged according to a spatial arrangement in which at least some of the elements of transducers are arranged along circles.

The specification is relative to a method for predicting that a subject is at risk of suffering from an obesity related disease, the method for predicting at least comprising a step of carrying out the steps of a method for post-processing images of the subject as previously described, to obtain determined parameters and a step of predicting that the subject is at risk of suffering from the obesity related disease based on the determined parameters, The specification also concerns a method for diagnosing an obesity related disease, the method for diagnosing at least comprising a step of carrying out the steps of a method for post-processing images of the subject as previously described, to obtain determined parameters, and a step of diagnosing the obesity related disease based on the determined parameters.

The specification describes a method for identifying a therapeutic target for preventing and/or treating an obesity related disease, the method comprising a step of carrying out the steps of a method for post-processing images of a first subject as previously described, to obtain first determined parameters, the first subject being a subject suffering from the obesity related disease, a step of carrying out the steps of a method for post-processing images of a second subject as previously described, to obtain second determined parameters, the second subject being a subject not suffering from the obesity related disease and a step of selecting a therapeutic target based on the comparison of the first and second determined parameters.

The specification is relative to a method for identifying a biomarker, the biomarker being a diagnostic biomarker of an obesity related disease, a susceptibility biomarker of an obesity related disease, a prognostic biomarker of an obesity related disease or a predictive biomarker in response to the treatment of an obesity related disease, the method comprising a step of carrying out the steps of a method for post-processing images of a first subject as previously described, to obtain first determined parameters, the first subject being a subject suffering from the obesity related disease, a step of carrying out the steps of the method for post-processing images of a second subject as previously described, to obtain second determined parameters, the second subject being a subject not suffering from the obesity related disease and a step of selecting a biomarker based on the comparison of the first and second determined parameters.

The specification describes a method for screening a compound useful as a probiotic, a prebiotic or a medicine, the compound having an effect on a known therapeutical target, for preventing and/or treating an obesity related disease, the method comprising a step of carrying out the steps of a method for post-processing images of a first subject as previously described, to obtain first determined parameters, the first subject being a subject suffering from the obesity related disease and having received the compound, a step of carrying out the steps of the method for post-processing images of a second subject as previously described, to obtain second determined parameters, the second subject being a subject suffering from the obesity related disease and not having received the compound and a step of selecting a compound based on the comparison of the first and second determined parameters.

The method also comprises the use of a method for post-processing images as previously described in:
   a method for predicting that a subject is at risk of suffering from an obesity related disease, the method for predicting comprising at least the steps of:
      carrying out the steps of the method for post-processing images of the subject, to obtain determined parameters, and
      predicting that the subject is at risk of suffering from the obesity related disease based on the determined parameters,
   a method for diagnosing an obesity related disease, the method for diagnosing at least comprising at least the steps of:
      carrying out the steps of the method for post-processing images of the subject, to obtain determined parameters, and
      diagnosing the obesity related disease based on the determined parameters,
   a method for identifying a therapeutic target for preventing and/or treating an obesity related disease, the method comprising at least the steps of:
      carrying out the steps of the method for post-processing images of a first subject, to obtain first determined parameters, the first subject being a subject suffering from the obesity related disease, and
carrying out the steps of the method for post-processing images of a second subject, to obtain second determined parameters, the second subject being a subject not suffering from the obesity related disease,
selecting a therapeutic target based on the comparison of the first and second determined parameters,
a method for identifying a biomarker, the biomarker being a diagnostic biomarker of an obesity related disease, a susceptibility biomarker of an obesity related disease, a prognostic biomarker of an obesity related disease or a predictive biomarker in response to the treatment of an obesity related disease, the method comprising at least the steps of:
carrying out the steps of a method for post-processing images of a first subject, to obtain first determined parameters, the first subject being a subject suffering from the obesity related disease,
carrying out the steps of the method for post-processing images of a second subject, to obtain second determined parameters, the second subject being a subject not suffering from the obesity related disease, and
selecting a biomarker based on the comparison of the first and second determined parameters, and
a method for screening a compound useful as a probiotic, a prebiotic or a medicine, the compound having an effect on a known therapeutical target, for preventing and/or treating an obesity related disease, the method comprising at least the steps of:
carrying out the steps of a method for post-processing images of a first subject, to obtain first determined parameters, the first subject being a subject suffering from the obesity related disease and having received the compound,
carrying out the steps of the method for post-processing images of a second subject, to obtain second determined parameters, the second subject being a subject suffering from the obesity related disease and not having received the compound, and
selecting a compound based on the comparison of the first and second determined parameters.

It is also proposed a method for treating a subject suffering from an obesity related disease, the method comprises a step of carrying out the steps of a method for measuring as previously described or the steps of a method for post-processing as previously described.

The specification describes a computer program product comprising program instructions, the comprising computer program instructions, the computer program instructions being loadable into a data-processing unit and adapted to cause execution at least one step of the method as previously described or implied in a use as previously described when run by the data-processing unit.

The specification also relates to a computer readable medium having encoded thereon computer program instructions which, when executed by a data-processing unit, cause execution at least one step of a method as previously or implied in a use as previously described.

It is also proposed a device for measuring at least one parameter of a region of interest of an organ of a subject, the organ being preferably the liver, one parameter being the global speed of sound in the region of interest, the global speed of sound in the region of interest being the integration of the speed of sound at several depths of the region of interest, the speed of sound at a given depth being named a local speed of sound, the device comprising an ultrasound probe comprising a set of elements of transducer, at least some of the elements of transducer being arranged along circles, the ultrasound probe being adapted to apply several ultrasound pulses, and to obtain over time several backscattered echoes from the region of interest corresponding to several excitations of the region of interest by ultrasound pulses applied with an ultrasound probe. The device for measuring further comprises a unit for controlling the relative movement of the ultrasound probe and the region of interest between each excitation, optionally, a sensor adapted to measure at least another physical value which is chosen in the group consisting of a value representative of stiffness, a value representative of deformation, the shear viscosity, the contractility, the degree of anisotropy of the fibers comprised in the region of interest and the direction of the fibers comprised in the region of interest. The device for measuring further comprises a calculator adapted to choose an assumed value for the speed of sound to be measured, calculate correlation coefficients of at least one backscattered echoes by using the assumed value, a correlation coefficient being equal to the correlation between the echo signal backscattered by a region of the tissue and received by a first element of transducer and the echo backscattered by the same region and received by a second element of transducer positioned at a given distance from the first element of transducer, the correlation coefficients being calculated for several pairs of elements of transducer corresponding to several distances. The calculator is further adapted to iterate the choosing step and the calculating step for several assumed values for the speed of sound to be measured, and determine the global speed of sound to be measured based on applying an optimization criteria on the calculated correlation coefficients obtained for each assumed values for the speed of sound to be measured.

BRIEF DESCRIPTION OF THE DRAWINGS

The invention will be better understood on the basis of the following description which is given in correspondence with the annexed figures and as an illustrative example, without restricting the object of the invention. In the annexed figures.

DETAILED DESCRIPTION OF SOME EMBODIMENTS

Figure 1:
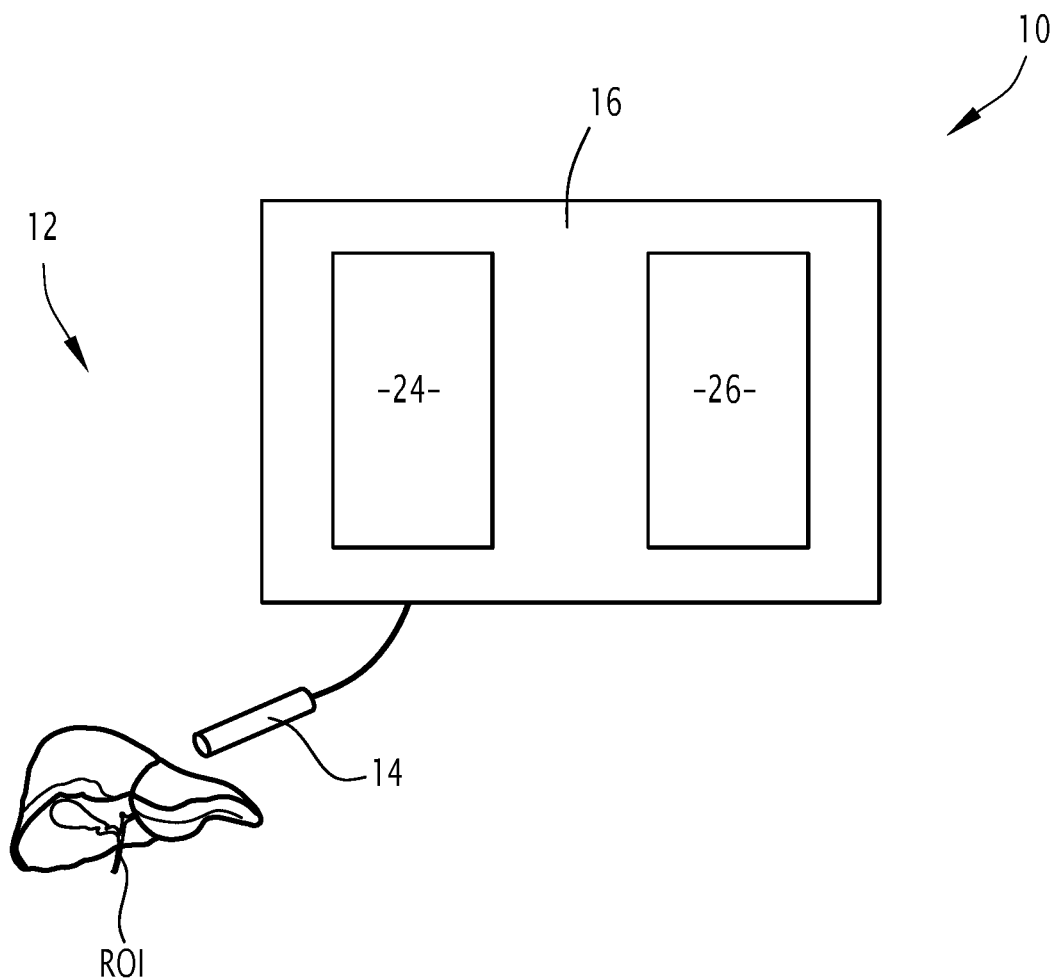
FIG. 1 shows schematically a device for measuring at least one parameter of a region of interest of the liver of a subject.

Description of a Device for Measuring at Least One Parameter of a Region of Interest
General Description of the Device for Measuring A device for measuring 10 at one parameter of a region of interest (ROI) of an organ 12 of a subject is represented on FIG. 1.

The device for measuring is adapted to measure several parameters among which the speed of sound in the ROI.

Other parameters include as a non-limitative list: a value representative of shear velocity or stiffness, a value representative of deformation, the shear viscosity, the contractility, the degree of anisotropy of the fibers comprised in the region of interest and the direction of the fibers comprised in the ROI or the fat content of the ROI.

The subject is usually human beings.

More generally, the subject is an animal, notably a vertebrate like a mammal, a bird or a rodent (notably a mouse).

As represented on FIG. 1, the device 12 for measuring comprises an ultrasound probe 14 and a controller 16.
Description of the Ultrasound Probe 14

The ultrasound probe 14 comprises a set of elements of transducer 18. Each element of transducer 18 is named element 18.

The set of elements 18 forms what is generally named as transducer.

Figure 2:
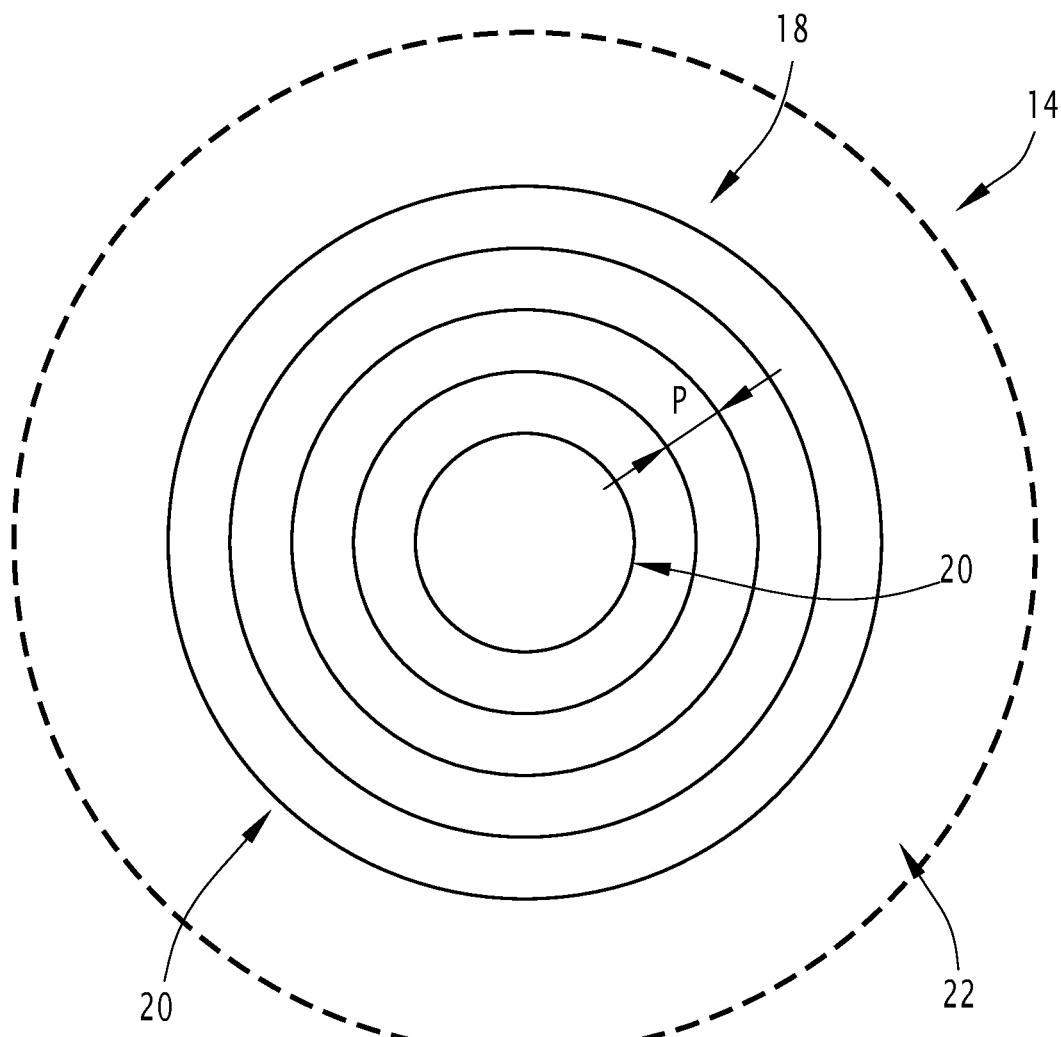
FIG. 2 illustrates an example of ultrasound probe which belongs to the device for measuring of FIG. 1 and comprises elements of transducer.

According to FIG. 2, the elements 18 are arranged along circles 20.

In this example, the circles 20 are concentric.

The number of circles 20 is equal to 5.

The circles 20 are spaced by a dimension named pitch P.

Each pitch P is inferior or equal to 0.5 millimeters.

This implies that the pitch P is inferior or equal to 5 times the ultrasound wavelengths at which the ultrasound probe 14 is adapted to operate.

As a typical example, the maximum ultrasound wavelength is taken, the wavelength corresponding to 0.1 millimeter.

Such condition enables to obtain a controlled electric impedance.

Preferably, the pitch P is inferior or equal to 3 times the ultrasound wavelengths at which the ultrasound probe 14 is adapted to operate.

Preferably, the pitch P is the same between the circles.

The set of elements 18 are arranged on a face 22 which has a disk shape.

In this example, the diameter of the disk is equal to 18 millimeters (mm).

More generally, the diameter of the disk is comprised between 10 mm and 25 mm.

The total number of elements 18 is comprised between 3 and 64.

Preferably, the total number of elements 18 is inferior to 40, preferably inferior to 20.
Description of the Controller 16

The controller 16 comprises a command unit 24 and a calculator 26 as two separate elements.

In variant, the command unit 24 and the calculator 26 may be a unique element.

The command unit 24 is adapted to control the set of elements 18 for applying several ultrasound pulses in the region of interest.

For this, the command unit 24 is adapted to apply electronic delays.

The command unit 24 is further adapted to command the ultrasound probe 14 to receive the backscattered echoes from the ROI.

The calculator 26 is adapted to receive the images of the region of interest from the ultrasound probe 14.

The calculator 26 is also adapted to apply post-processings on the images so as to determine parameters relative to the ROI.

In the illustrated case, the parameters include at least the speed of sound in the ROI.

The calculator 26 is adapted to calculate, for each distance between two pairs of elements 18, the spatial cross-correlation function of the backscattered echoes received by each pair of elements 18 situated at a given distance.

The calculator 26 is adapted to deduce the speed of sound in the region of interest based on the calculated cross-correlation functions.

Figure 3:
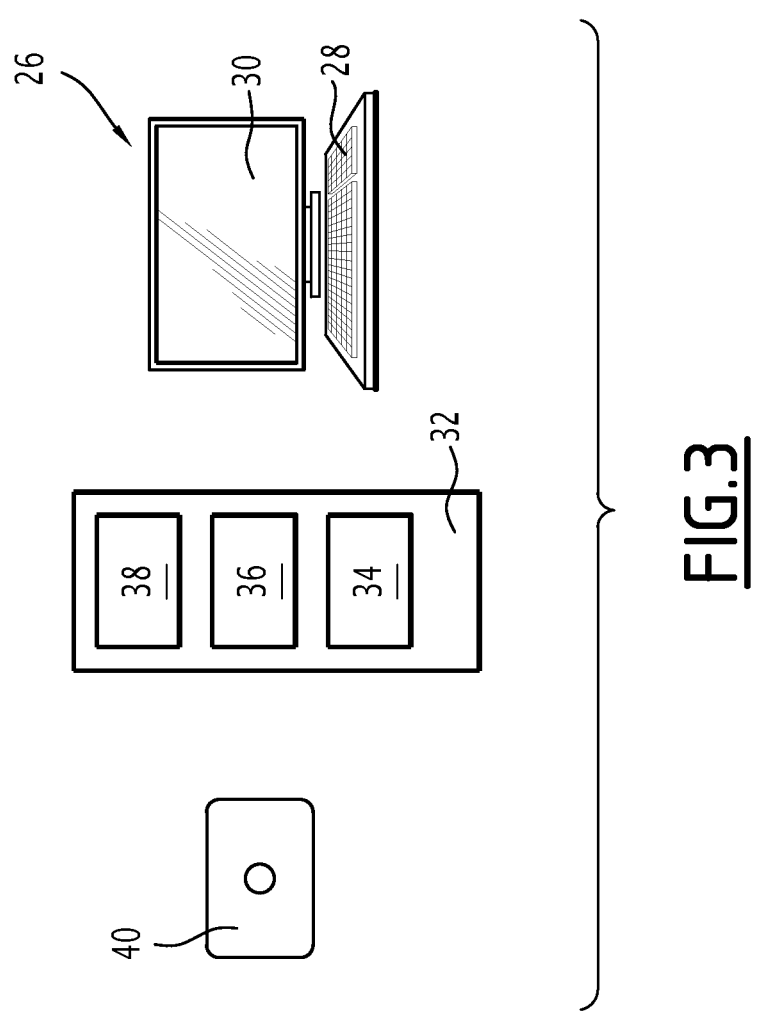
FIG. 3 shows schematically a calculator which is part of the device for measuring of FIG. 1.

According to the embodiment of FIG. 3, the calculator 26 is such that the interaction between a computer program product and the calculator 26 enables to carry out a method for post-processing images. The method for post-processing images is thus a computer-implemented method.

The calculator 26 is a desktop computer. In variant, the system is a rack-mounted computer, a laptop computer, a tablet computer, a Personal Digital Assistant (PDA) or a smartphone.

In specific embodiments, the computer is adapted to operate in real-time and/or is an embedded system, notably in a vehicle such as a plane.

In the case of FIG. 3, the calculator 26 comprises a processor 32, a user interface and a communication device (not represented).

The processor 32 is electronic circuitry adapted to manipulate and/or transform data represented by electronic or physical quantities in registers of the system X and/or memories in other similar data corresponding to physical data in the memories of the registers or other kinds of displaying devices, transmitting devices or memoring devices.

As specific examples, the processor 32 comprises a monocore or multicore processor (such as a central processing unit (CPU), a graphics processing unit (GPU), a microcontroller and a Digital Signal Processor (DSP)), a programmable logic circuitry (such as an Application Specific Integrated Circuit (ASIC), a Field Programmable Gate Array (FPGA), a Programmable Logic Device (PLD) and programmable logic arrays (PLA)), a state machine, gated logic and discrete hardware components.

The processor 32 comprises a data-processing unit 34 which is adapted to process data, notably by carrying out calculations, memories 36 adapted to store data and a reader 38 adapted to read a computer readable medium.

The user interface comprises an input device 28 and an output device 30.

The input device 28 is a device enabling the user of the calculator 26 to input information or command to the calculator 26.

In FIG. 3, the input device 28 is a keyboard. Alternatively, the input device 28 is a pointing device (such as a mouse, a touch pad and a digitizing tablet), a voice-recognition device, an eye tracker or an haptic device (motion gestures analysis).

The output device 30 is a graphical user interface, that is a display unit adapted to provide information to the user of the calculator 26.

In FIG. 3, the output device 30 is a display screen for visual presentation of output.

In other embodiments, the output device is a printer, an augmented and/or virtual display unit, a speaker or another sound generating device for audible presentation of output, a unit producing vibrations and/or odors or a unit adapted to produce electrical signal.

In a specific embodiment, the input device 28 and the output device 30 are the same component forming man-machine interfaces, such as an interactive screen.

The communication device enables unidirectional or bidirectional communication between the components of the calculator 26. For instance, the communication device is a bus communication system or a input/output interfaces.

The presence of the communication device enables that, in some embodiments, the components of the calculator 26 be remote one from another.

The computer program product comprises a computer readable medium 40.

The computer readable medium 40 is a tangible device that can be read by the reader 34 of the processor 32.

Notably, the computer readable medium 40 is not transitory signals per se, such as radio waves or other freely propagating electromagnetic waves, such as light pulses or electronic signals.

Such computer readable storage medium 40 is, for instance, an electronic storage device, a magnetic storage device, an optical storage device, an electromagnetic storage device, a semiconductor storage device or any combination thereof.

As a non-exhaustive list of more specific examples, the computer readable storage medium 40 is a mechanically encoded device such a punchcards or raised structures in a groove, a diskette, a hard disk, a read-only memory (ROM), a random access memory (RAM), an erasable programmable read-only memory (EROM), electrically erasable and programmable read only memory (EEPROM), a magnetic-optical disk, a static random access memory (SRAM), a compact disc read-only memory (CD-ROM), a digital versatile disk (DVD), a memory stick, a floppy disk, a flash memory, a solid state drive disk (SSD) or a PC card such as a Personal Computer Memory Card International Association (PCMCIA).

A computer program is stored in the computer readable storage medium 40. The computer program comprises one or more stored sequence of program instructions.

Such program instructions when run by the data-processing unit 34, cause the execution of steps of the method for post-processing images.

For instance, the form of the program instructions is a source code form, a computer executable form or any intermediate forms between a source code and a computer executable form, such as the form resulting from the conversion of the source code via an interpreter, an assembler, a compiler, a linker or a locator. In variant, program instructions are a microcode, firmware instructions, state-setting data, configuration data for integrated circuitry (for instance VHDL) or an object code Program instructions are written in any combination of one or more languages, such as an object oriented programming language (FORTRAN, C++, JAVA, HTML), procedural programming language (language C for instance).

Alternatively, the program instructions are downloaded from an external source through a network as it is notably the case for applications. In such case, the computer program product comprises a computer-readable data carrier having stored thereon the program instructions or a data carrier signal having encoded thereon the program instructions.

In each case, the computer program product comprises instructions which are loadable into the data-processing unit 34 and adapted to cause execution of the method for post-processing images when run by the data-processing unit 34. According to the embodiments, the execution is entirely or partially achieved either on the calculator 26, that is a single computer, or in a distributed system among several computers (notably via cloud computing).

Description of an Example of Use of the Device for Measuring

Figure 4:
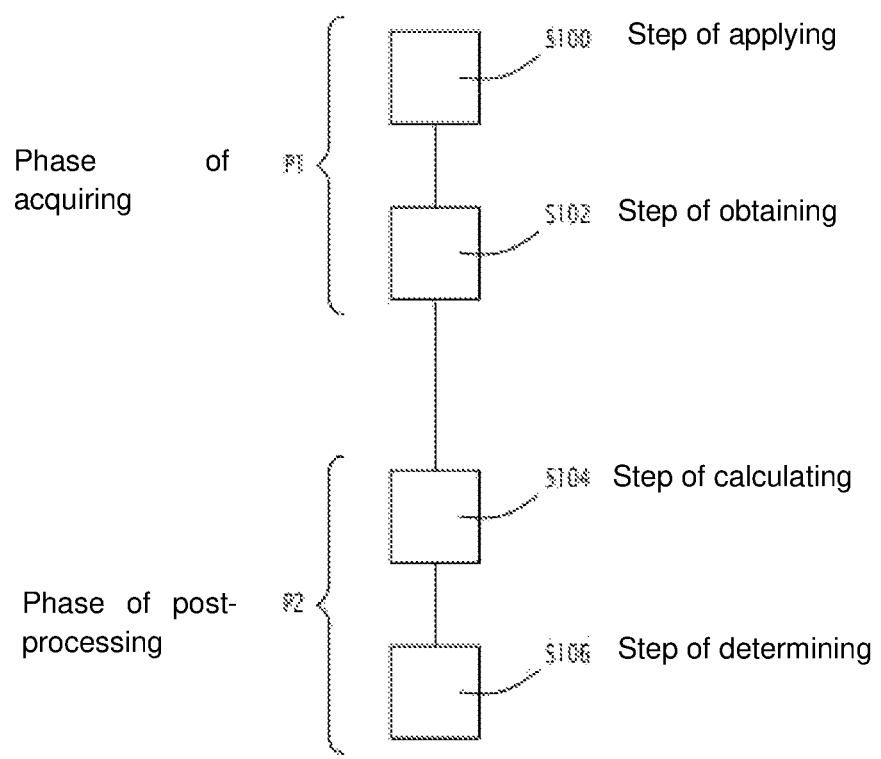
FIG. 4 shows a flowchart of an example of carrying out a method for measuring at least one parameter in the liver, among which the speed of sound.

Operation of the device 10 is now described by illustrating an example of carrying out the method for measuring as illustrated by the flowchart of FIG. 4.

The method for measuring is a method for measuring at least one parameter of a region of interest of an organ of a subject, one parameter being the global speed of sound in the region of interest.

The global speed of sound in the region of interest is the integration of the speed of sound at several depths of the region of interest.

In what follows, the speed of sound at a given depth is named a local speed of sound.

By this definition, it is meant that the global speed of sound is the integral of local speed of sound between two depths corresponding to the limit values between which the integral is calculated.

As apparent on FIG. 4, the method for measuring comprises two phases: a first phase of acquiring P1 and a second phase of post-processing P2.

On the phase of acquiring P1 The phase of acquiring P1 comprises a step of applying S100 and a step of obtaining S102.

At the step of applying S100, several ultrasound pulses are applied by the ultrasound probe 14.

These applied ultrasound pulses correspond to several excitations.

According to a specific embodiment, the number of excitations within the ROI is superior to 10.

According to this example, the ultrasound pulses which are applied are focused in the ROI at different times but this is not mandatory.

In reaction to the excitation by the applied ultrasound pulses, the diffusers of the ROI scatter the ultrasound pulses in various directions and notably backwards towards the ultrasound probe 14. The diffusers are randomly distributed in the ROI. The term "backscatter" is often used for these echoes coming from the diffusers.

At the step of obtaining S102, the backscattered echoes from the ROI are received over time by the ultrasound probe 14.

In other words, the step of obtaining S102 is a step wherein several backscattered echoes from the region of interest corresponding to several excitations of the region of interest by ultrasound pulses applied with an ultrasound probe 14 are obtained over time.

On the Phase of Post-Processing P2

The phase of post-processing P2 comprises a step of calculating S104 and a step of determining S106.

The phase of post-processing P2 is achieved by the calculator 26.

Before detailing the operations carried out during the different steps of calculating S104 and determining S106, it should be explained how the spatial coherence properties of ultrasound waves are used during the phase of post-processing P2.

The similarity between the signals received by two distant elements 18 of the ultrasound probe 14 characterizes the spatial coherence of the received wavefield. Van Cittert and Zernike determined the degree of coherence by defining a coherence function as the averaged cross-correlation between two signals received at two points of space. The Van Cittert-Zernike theorem states that the coherence function is the spatial Fourier transform of the intensity distribution at the focus.

By calculating autocorrelations between all pairs of receiver elements, the coherence function R is assessed as a function of distance between elements 18 according to the following formula:

$$R(m) = \frac{N}{N-m} \cdot \frac{\sum_{k=1}^{N-m} c(i, i+m)}{\sum_{k=1}^{N} c(i, i)}$$

where:
m is the distance between elements 18 normalized to the size of the elements 18,
N is an integer representing the total number of elements 18 in the ultrasound probe 14, and
c(i,j) is defined as $c(i,j) = \Sigma_{T1}^{T2}(S_i(t) - \overline{S}_i)(S_j(t) - \overline{S}_j)$ with:
  $S_i$ the time-delayed ultrasound signal received by the element 18 having the same index i as the signal,
  S being the conjugate of the ultrasound signal, and
  [T1;T2] is the temporal window centered on the focal time.

When the ultrasonic wave is focused on a point-like target in the medium, the coherence function is equal to 1 all along the ultrasound probe 14. In the case of a homogeneous medium made of randomly distributed Rayleigh scatterers, the degree of coherence decreases as the distance between the elements 18 increases.

Therefore, a focused beam generated by a rectangular aperture will lead to a triangle coherence function of backscattered echoes coming from a random distribution of Rayleigh scatterers in the focal spot.

For a fixed depth, if the speed of sound used for focusing in the homogeneous random medium is under- or overestimated, then the focal spot size at the desired depth will increase, leading to a dramatic decrease of coherence.

In other words, to evaluate spatial coherence, the ultrasonic signals received on each element 18 of the ultrasound probe 14 coming from the focal spot are realigned and their degree of similarity is quantified.

This quantification is called the coherence function.

When the degree of similarity (or coherence) is represented as a function of the element distance, it is known to be a triangle provided the medium is a random medium. Liver is a random medium.

As an example, two signals received from two elements 18 side-by-side will have a higher degree of similarity than two signals received from two opposite elements 18.

This phenomenon is due to the fact that the travel path of the waves coming from the focal spot is very similar when arriving to the two side-by-side elements 18 but strongly differs in the opposite element 18 case.

To realign the ultrasonic signals, the travel time of the waves is calculated using their travel path and their speed.

The travel path depends on geometric parameters such as the distance to the focal spot and the element positions.

Therefore, the only unknown parameter remains the speed.

Thus, the coherence function is calculated around the focal spot on the ultrasound axis for different speed of sound.

The speed of sound for which the coherence function integral is the largest is thus the "true" speed of sound of the medium.

It has been shown that there is a link between the spatial coherence function and the speed of sound via the Van Cittert-Zernike theorem.

This principle is used in the two steps of phase of post-processing P2.

The step of calculating S104 comprises three substeps: a first substep of choosing, a second substep of calculating and a third substep of iterating.

At the first substep, an assumed value for the speed of sound to be measured is chosen.

At the second substep, correlation coefficients of at least one backscattered echoes by using the assumed value are calculated.

A correlation coefficient is equal to the correlation between the echo signal backscattered by a region of the tissue and received by a first element of transducer 18 and the echo backscattered by the same region and received by a second element of transducer 18 positioned at a given distance from the first element 18.

The correlation coefficients are calculated for several pairs of elements 18 corresponding to several distances.

Such second substep can be carried out according to several calculation techniques. According to a first calculation technique, it is first established a spatial coherence function corresponding to the evolution of the value of the correlation coefficients with distance for each backscattered echoes.

Second, a statistical estimator is applied to the established spatial coherence functions to obtain a mean spatial coherence function.

For instance, a statistical estimator is a mean operator.

According to a second calculation technique, a statistical estimator is applied to the correlation coefficients calculated at the same distance for several received backscattered echoes to obtain mean correlation coefficients.

At the third substep, iterations of the first substep and second substep are carried out.

These first substep and second substep are iterated for several assumed values of the speed of sound to be measured.

The number of assumed values is, for instance, superior to 10 and inferior to 20.

At the step of determining S106, the global speed of sound to be measured is determined based on applying an optimization criteria on the calculated correlation coefficients obtained for each assumed values for the speed of sound to be measured.

As a first example, the optimization criteria is maximizing the autocorrelation function.

Such criteria can be construed as a maximization of the area which corresponds to the integral of the coherence function.

In variant, the optimization criteria is maximizing the coherence factor.

By definition, the coherence factor is proportional to the ratio of the coherent ultrasound energy received by the ultrasound probe 14 and the incoherent ultrasound energy received by the ultrasound probe 14.

At the end of the step of determining S106, the speed of sound in the ROI is obtained based on the calculated cross-correlation functions.

Advantages of the Proposed Method

The method analyzes the spatial coherence function of backscattered echoes resulting from an interaction of ultrasound beams with the ROI to obtain the speed of sound in the medium.

The method enables to obtain a more precise determination of the speed of sound in the ROI.

In addition, the method is a non-invasive method that can be carried out at any depth of the liver.

The method only uses a relatively low number of elements 18. Indeed, the number is inferior to 40.

This implies that a more compact device 12 can be designed.

Therefore, the device 12 is portable.

Additionally, the method implies lower cost to be carried out.

The method can be achieved at a relatively high pace.

The method enables to obtain a better measurement of the speed of sound in soft tissues.

Indeed, the design of the ultrasound probe 14 enables dynamic focusing along the depth axis. By contrast, in the prior art, the ultrasound probe 14 has a fixed elevation focusing depth.

A fixed focusing depth results in a calculation of the speed of sound which is only correct for this focusing depth.

The method also enables to deal with the aberration caused by intercostal layers in the liver without additional techniques.

Indeed, the attainment of an optimal coherence function is possible in a perfectly homogeneous medium with a constant speed of sound. However, sound speed heterogeneities in the intercostal space of difficult patients result in phase aberrations along the travel path of the ultrasonic beam. In other words, intercostal layers act as near field phase aberrator.

This issue is circumvented in this case by the specific ultrasound probe 14 that is used, this ultrasound probe 14 enabling to obtain a focusing at several depths in the liver.

Indeed, each depth corresponds to a different speed of sound, the evolution of the speed of sound is directly linked to the evolution of the aberrations.

Applications of the Proposed Method

Such a precision in evaluating the speed of sound in the liver can be used to characterize the fat content in liver.

Indeed, the speed of sound varies with the fat content in soft tissues. The speed of sound within soft tissues is known to vary slightly from muscle (1575 m.s$^{-1}$) to fat (1450 m.s$^{-1}$).

The method can thus be used for quantification of liver fat content in real time.

One example of such quantification can be found in the article entitled 'Ultrasonic fat fraction quantification using in vivo adaptive sound speed' by Marion Imbault et al. 2018 Phys. Med. Biol. 63 215013.

The method can also be used for determining the liver fat content in a set of images that is provided.

Such determination corresponds to a method for post-processing images of the ROI to obtain determined parameters wherein only the phase for post-processing P2 is carried out.

The method for post-processing may then comprise a step of quantifying the fat content of the liver by using the determined speed of sound.

The determined parameters may then be used for pre-clinical or clinical assessments.

Examples of such assessments are given below by using the fact that the quantification of liver fat content is directly linked to steatosis which is implied in the obesity related disease.

The obesity related diseases encompass the cancer, the steatoses, the type 2 diabetes, heart disease, non-alcoholic fatty liver disease (NAFLD) and nonalcoholic steatohepatitis (NASH) which is the most severe form of NAFLD.

Thus, by enabling to access to the fat content, such method can be used in pre-clinical or clinical assessments relative to obesity related diseases.

According to a first example, it can be proposed a method for predicting that a subject is at risk of suffering from an obesity related disease, the method for predicting at least comprising the step of carrying out the steps of the method for post-processing images of the subject, to obtain determined parameters and predicting that the subject is at risk of suffering from the obesity related disease based on the determined parameters.

According to a second example, a method for diagnosing an obesity related disease can be considered. The method for diagnosing at least comprises the step of carrying out the steps of the method for post-processing images of the subject, to obtain determined parameters and diagnosing the obesity related disease based on the determined parameters.

According of a third example, it can be proposed a method for identifying a therapeutic target for preventing and/or treating an obesity related disease. Such method for identifying comprises the step of carrying out the steps of the method for post-processing images of a first subject, to obtain first determined parameters, the first subject being a subject suffering from the obesity related disease. The method for identifying also comprises a step of carrying out the steps of the method for post-processing images of a second subject, to obtain second determined parameters, the second subject being a subject not suffering from the obesity related disease. The method for identifying also comprising a step of selecting a therapeutic target based on the comparison of the first and second determined parameters.

According to a fourth example, a method for identifying a biomarker, the biomarker being a diagnostic biomarker of an obesity related disease, a susceptibility biomarker of an obesity related disease, a prognostic biomarker of an obesity related disease or a predictive biomarker in response to the treatment of an obesity related disease can be considered. The method for identifying comprises a step of carrying out the steps of a method for post-processing images of a first subject, to obtain first determined parameters, the first subject being a subject suffering from the obesity related disease, a step of carrying out the steps of the method for post-processing images of a second subject, to obtain second determined parameters, the second subject being a subject not suffering from the obesity related disease and a step of selecting a biomarker based on the comparison of the first and second determined parameters.

According to a fifth example, it also proposed a method for screening a compound useful as a probiotic, a prebiotic or a medicine, the compound having an effect on a known therapeutical target, for preventing and/or treating an obesity related disease. The method for screening comprises the step of carrying out the steps of the method for post-processing images of a first subject, to obtain first determined parameters, the first subject being a subject suffering from the obesity related disease and having received the compound. The method for screening further comprises a step of carrying out the steps of the method for post-processing images of a second subject, to obtain second determined parameters, the second subject being a subject suffering from the obesity related disease and not having received the compound. The method for screening also comprises a step of selecting a compound based on the comparison of the first and second determined parameters.

Extension of the previous assessment methods can also be considered.

Notably, it should be noted that steatosis is mainly associated with liver which is the primary organ that is concerned with such phenomenon. However, steatosis may concern any organ like the kidneys or the heart.

Therefore, such assessment methods may be applied to ROIs which are not in the liver but in any organ such as the kidneys or the heart.

Such assessment methods may be used for any organ located in the abdomen, the heart or the brain (notably the baby's brain).

The method for measuring the speed of sound may also be used to determine the evolution of sound speed in the superficial layer of the ROI.

A specific example of such application is a case wherein the organ comprises a tissue structure and the propagation of sound in the tissue structure with depth is modeled by a layered model comprising several layers with depth. In such case, the method for measuring further comprises deducing several local speeds of sound of the region of interest from several global speeds of sound by using the layered model, the global speeds of sound being measured for respective depths, said depths comprising at least one depth per layer of the layered model.

This is notably interesting when the region of interest is the liver and at least one layer of the layered model comprises the skin situated between the liver and the ultrasound probe 14.

Determining Other Values

The method may also be used for determining other physical values.

For instance, the apparatus 10 for analyzing may be further adapted for obtaining at least one functional parameter of the ROI.

By definition, a functional parameter is a parameter relative to the properties of the muscle, a parameter relative to the metabolism of the ROI or a parameter relative to the operation of the ROI.

For this, the calculator 26 of the apparatus 10 determines a first plurality of values representative of stiffness values of at least one part of the parts of the muscle at a first plurality of times by using the collected ultrasound waves, the first plurality of times being included in the plurality of times.

A value is representative of stiffness is any physical quantity linked to the stiffness.

For instance, the shear modulus $\mu$ of the ROI is a value representative of stiffness. As shear waves propagate in a muscle in an anisotropic way, such shear modulus E is a mean value of several shear modulus $\mu_{direction}$ of the ROI along several directions.

Alternatively, the shear modulus $\mu_{direction}$ of the ROI in a specific direction is also a value representative of stiffness. The shear modulus which is along the direction of the fibers of the ROI labeled $\mu_{parallel}$ and the shear modulus which is along the direction perpendicular to the direction of the fibers of the ROI labeled $\mu_{perpendicular}$ are examples of shear modulus of the ROI in a specific direction.

As another example, the Young's modulus E of the ROI is a value representative of stiffness. By definition, the Young's modulus E is linked to the shear modulus $\mu$ by the relation $E=3\mu$. As shear waves propagate in a muscle in an anisotropic way, such Young's modulus $\mu$ is a mean value of several Young's modulus $E_{direction}$ of the myocardium along several directions.

Alternatively, the Young's modulus $E_{direction}$ of the ROI in a specific direction is also a value representative of stiffness. The Young's modulus which is along the direction of the fibers of the ROI labeled $E_{parallel}$ and the Young's modulus which is along the direction perpendicular to the direction of the fibers of the ROI labeled $E_{perpendicular}$ are examples of Young's modulus of the ROI in a specific direction.

As another example, the propagation speed $c_s$ of shear waves in the ROI is a value representative of stiffness. The propagation speed $c_s$ of shear waves in the ROI is linked to the Young's modulus $E_{direction}$ by the following relation:

$$c_S = \sqrt{\frac{E}{3\rho}}$$

wherein $\rho$ is the density of the myocardium.

As shear waves propagate in a muscle in an anisotropic way, such propagation speed $c_s$ of shear waves in the ROI is a mean value of several propagation speeds $c_{s\_direction}$ of shear waves in the ROI along several directions.

Alternatively, the propagation speed $c_{s\_direction}$ of shear waves in the ROI in a specific direction is also a value representative of stiffness. The propagation speed of shear waves along the direction of the fibers in the ROI labeled $c_{s\_parallel}$ and the propagation speed of shear waves along the direction perpendicular to the direction of the fibers in the ROI labeled $c_{s\_perpendicular}$ are examples of propagation speed $c_{s\_direction}$ of shear waves in the ROI in a specific direction.

The calculator 26 determines a second plurality of values representative of deformation values of said part at a second plurality of times by using the collected ultrasound waves, the second plurality of times being included in the plurality of times and being associated with the first plurality of times in a one-to-one relationship.

A value is representative of deformation is any physical quantity linked to the deformation.

The cumulative deformation is an example of value representative of deformation.

The length of the segment is an example of value representative of deformation.

Such length is measured along any direction. The length along the direction of the fibers, the length along the direction perpendicular to the direction of the fibers are specific examples of length of the segment which may be considered.

The length of the segment which is normalized to a reference length is another example of value representative of deformation.

The volume of the ventricle is also representative of the deformation.

The second plurality of times is included in the plurality of times and is associated with the first plurality of times in a one-to-one relationship.

Preferably, the absolute value of the difference between a time of the first plurality of times and the associated time of the second plurality of times below or equal to 100 milliseconds modulo the temporal duration of the cardiac cycle.

The calculator 26 then deduces at least one myocardium functional parameter based on the first plurality of values and the second plurality of values.

According to an example, the functional parameter of the ROI is representative of the mechanical work of the segment. In such case, the functional parameter is obtained by calculating the area of the stiffness-deformation loop.

Other measurement can be considered such as the shear viscosity, the contractibility, the degree of anisotropy of the fibers of a ROI and the direction of the fibers in the ROI.

This enables to obtain an measurement method of the ROI providing with additional parameters that can be advantageously used for the clinical or pre-clinical assessments.

Others Interesting Embodiments of the Method for Measuring

Improved Methods

As it may remain residual aberrations, the method for measuring the speed of sound may comprises techniques for taking into account the aberrations.

A technique implying creating a virtual point-like reflector may be considered.

The method may also benefit from a high number of realizations of the calculation of the speed of sound so as to improve the robustness of the method.

Other Forms for the Ultrasound Probe 14

At last, it should be noted that other forms for the ultrasound probe 14 may provide the same advantages.

For instance, the elements 18 may be arranged along another form, such an ellipse.

Figure 5:
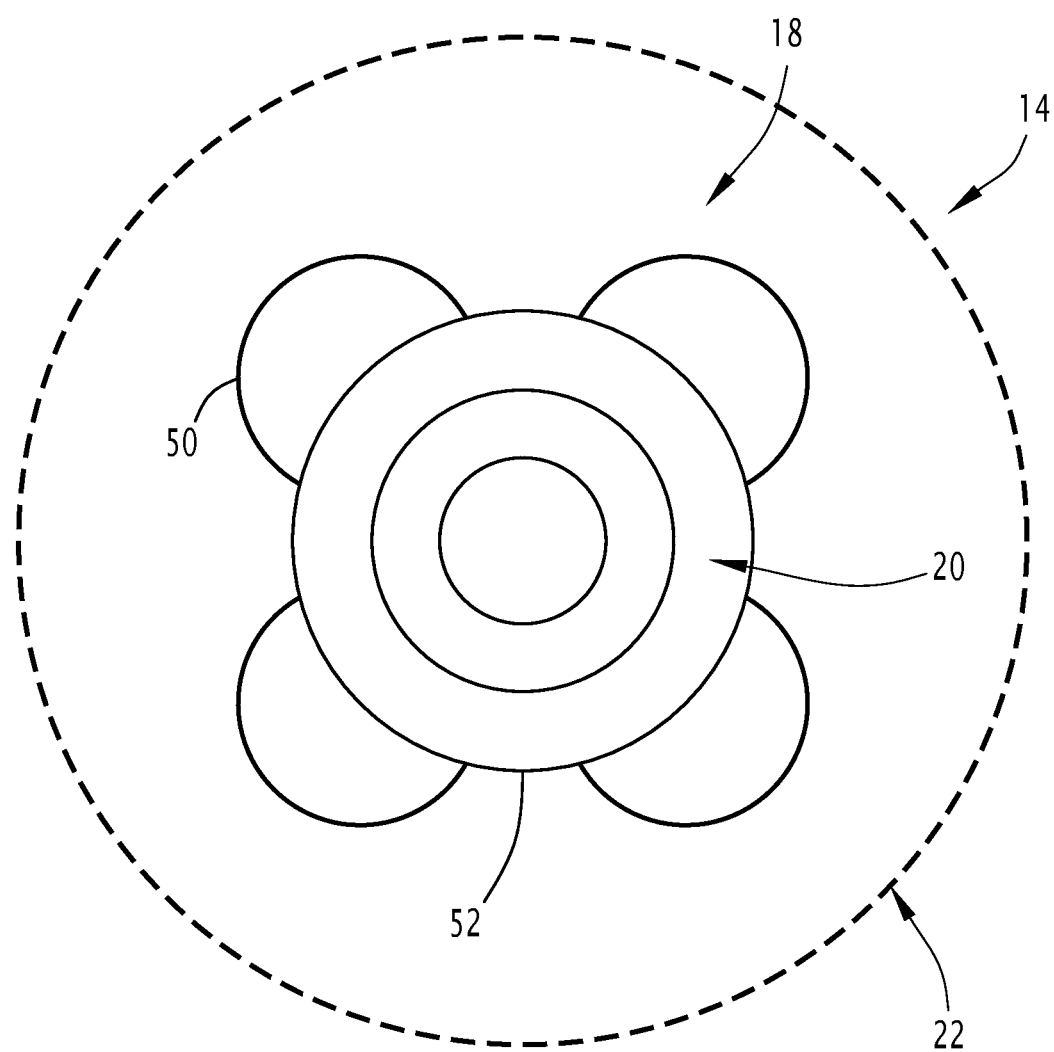
FIG. 5 illustrates another example of ultrasound probe which belongs to the device for measuring of FIG. 1.

Some elements 18 may also be arranged not along specific lines such as a "flower-configuration" illustrated in FIG. 5.

By definition, a "flower-configuration" is a configuration wherein some elements 18 are arranged along circles 20 and others are arranged along a portion of circles 50.

The portion of circles 50 are linked to the largest circles 52.

In the specific example of FIG. 5, the portions of circles 20 are arranged in a symmetrical way.

In addition, the number of portions of circles 50 is equal to 4 which leads to this flower-like configuration.

Figure 6:
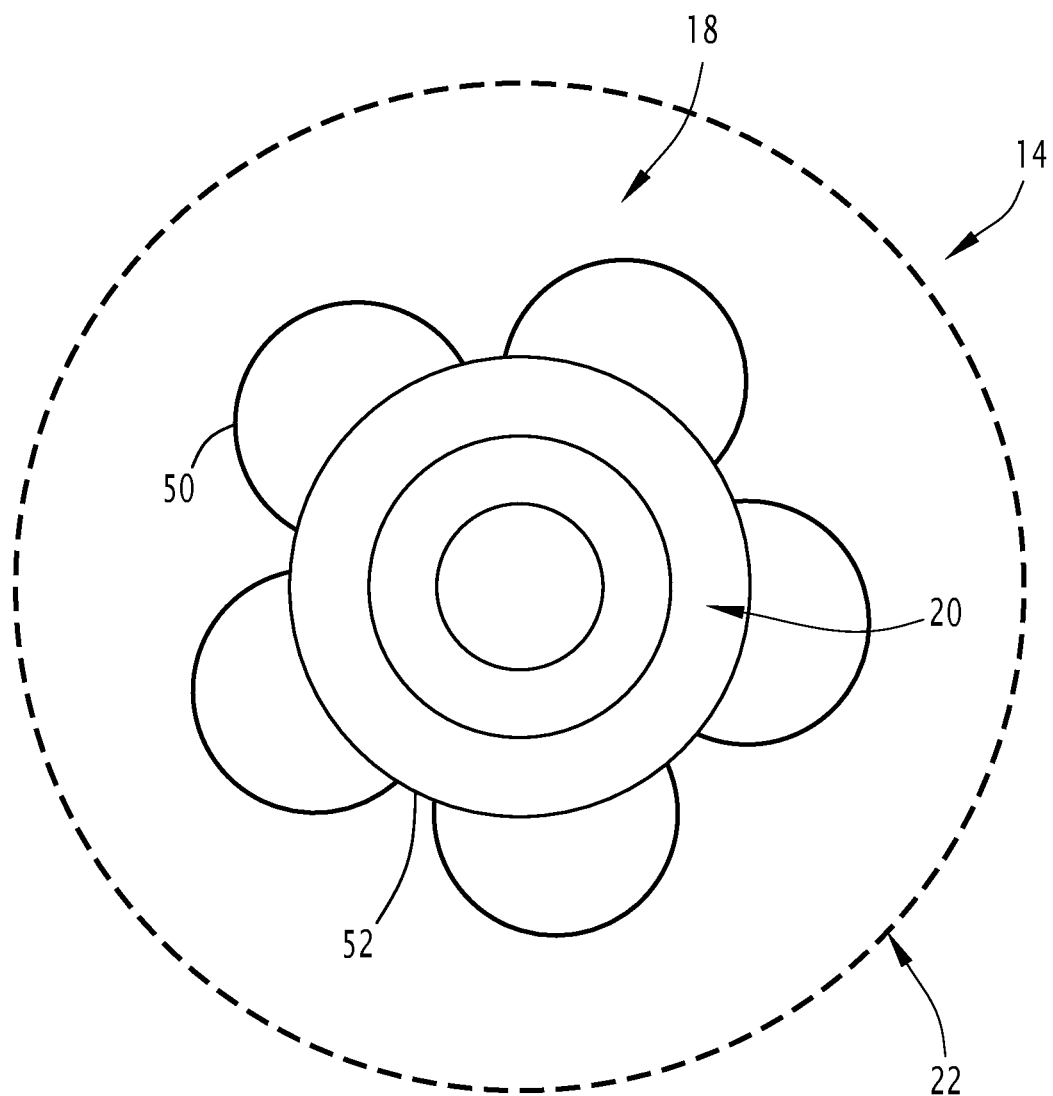
FIG. 6 shows another example of ultrasound probe which belongs to the device for measuring of FIG. 1.

In another configuration illustrated in FIG. 6, the number of portions of circles 50 is 5.

The number of portions of circles 50 is inferior or equal to 8.

Such configurations enable to carry out several measurements (corresponding to different physical values) with one ultrasound probe which confers desirable precision for the different measurements. Such measurements are detailed in the paragraph "determining other values".

Alternative Methods

It may also be considered that instead of using a specific ultrasound probe 14, a movement of the ultrasound probe 14 may provide with similar advantages as the previously described method for measuring the sound speed in the ROI.

In such case, the method for measuring sound speed in a region of interest in the ROI comprises the step of applying several ultrasound pulses with an ultrasound probe 14 comprising a set of elements 18, the ultrasound pulses being focused in the region at different time, the ultrasound probe 14 being moved between each application, the step of receiving the backscattered echoes from the region of interest.

These steps are followed by the phase for post-processing P2 with a step of, for each applied pulse, calculating, for each distance between two pairs of elements 18, the spatial cross-correlation function of the backscattered echoes received by each pair of elements 18 situated at a given distance, and a step for deducing the speed of sound in the region of interest based on the calculated cross-correlation functions.

More generally, the ultrasound probe 14 and the region of interest ROI are moved relatively to each other between each excitation.

For instance, the movement may be generated by the breathing of the subject.

So as to ensure that the relative movement is appropriate, several techniques can be considered either alone or in combination.

As a specific technique, the method comprises a step of measuring the value of the relative movement between the ultrasound probe 4 and the region of interest, the step of measuring being carried out by using an accelerometer.

Interacting with the user of the device for measuring 10 is another technique.

For instance, the method comprises a step of displaying data concerning the relative movement between two successive excitations.

As an illustration, the displayed data are data corresponding to the requirement that a minimum amplitude is strictly superior to an operating ultrasound wavelength defined for the ultrasound probe 14, the minimum amplitude being defined for the relative movement between two successive excitations.

Alternatively or in combination, the displayed data are data corresponding to the requirement that a maximum amplitude is strictly inferior to 20 millimeters, a maximum amplitude is defined for the relative movement between two successive excitations.

In still another embodiment, the displayed data are data which enables to determine whether the requirement that the relative movement between two successive excitations corresponds to an area having a surface superior to 10 mm$^2$ is fulfilled or not Alternatively or in combination, the obtaining step is automatically triggered by a sensor that detects the motion of the ultrasound probe.

The embodiments and alternative embodiments considered here-above can be combined to generate further embodiments of the invention.

Experimental Section

The experimental section is devoted to show experiments made by the Applicant and to discuss the obtained results.

The method was first validated by calibrated phantoms with known speed of sound.

It was then applied to the human liver of a healthy volunteer.

When displaying an example of realigning the ultrasonic signals with false and the true speed of sound of calibrated phantoms, it can be observed that for the "true" speed of sound, the ultrasonic signals received are better realigned than when the "false" speed of sound is applied.

Figure 7:
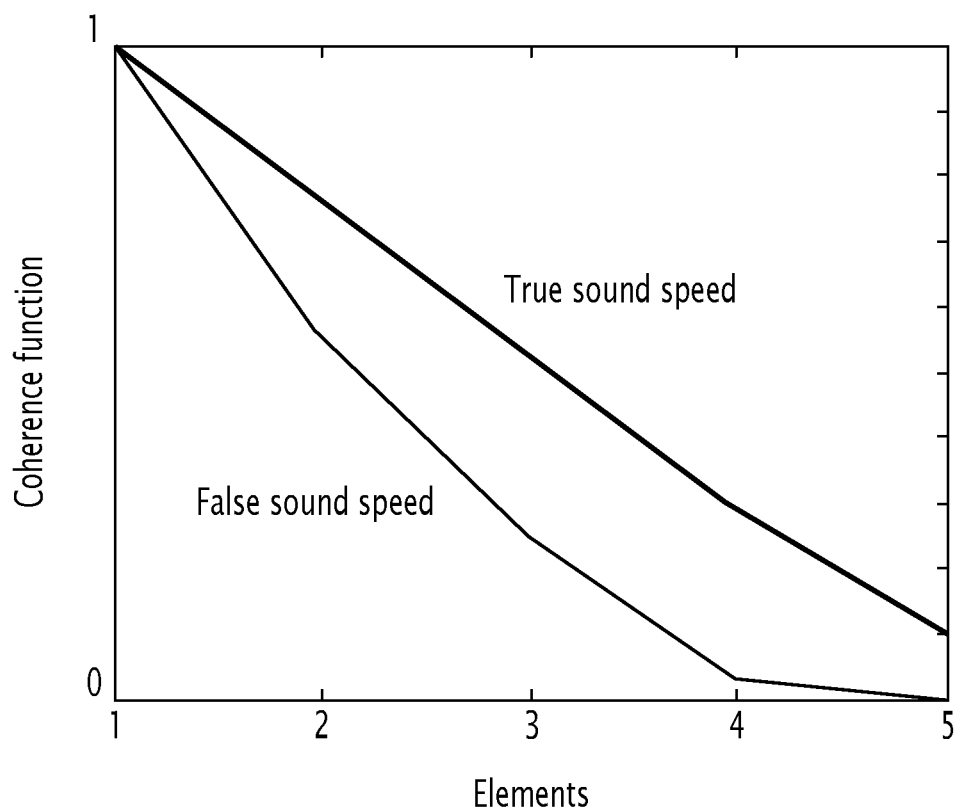
FIG. 7 illustrates the evolution of the coherence function with the elements of transducer.

FIG. 7 displays an example of the two coherence functions assessed in phantom for the false (curve in dot lines) and the true sound speed (curve in solid line).

Again, it appears that the case of the true speed corresponds to the area under the curve that is the larger.

The coherence function integral assessed in the liver of a human volunteer at a depth of 40 millimeters (mm) as a function of depth and speed of sound is displayed in FIG. 7.

A speed of sound of 1570 m.s$^{-1}$ was found.

With these experiments, the Applicant showed the feasibility of performing speed of sound measurements with a small device 12 in a healthy liver.

LIST OF ABBREVIATIONS

In the description, the following abbreviations are used:
MRI: magnetic resonance imaging
NAFLD: non-alcoholic fatty liver disease
NASH: nonalcoholic steatohepatitis
PDFF: proton-density fat fraction
ROI: region of interest

The invention claimed is:

1. A method for measuring at least one parameter of a region of interest of an organ of a subject, the at least one parameter being a global speed of sound in the region of interest, the global speed of sound in the region of interest being the integration of a speed of sound at several depths of the region of interest, the speed of sound at a given depth being named a local speed of sound, the method comprising at least the steps of:
    obtaining over time several backscattered echoes from the region of interest corresponding to several excitations of the region of interest by ultrasound pulses applied with an ultrasound probe, the ultrasound probe comprising a set of elements of transducer, the set of elements of transducer being arranged according to a spatial arrangement in which at least some of the elements of transducer are arranged along circles, wherein the set of elements of transducer are arranged according to a spatial arrangement in which some elements of the transducers are arranged along concentric circles and other elements of the transducer are arranged along additional portions of circles, the additional portions of circle extending between two extremities, each extremity belonging to a largest of the concentric circles,
    choosing an assumed value for the speed of sound to be measured,
    calculating correlation coefficients of at least one backscattered echo by using the assumed value, a correlation coefficient being equal to a correlation between an echo signal backscattered by a region of a tissue and received by a first element of transducer and the echo signal backscattered by the same region of the tissue and received by a second element of transducer positioned at a given distance from the first element of transducer, the correlation coefficients being calculated for several pairs of elements of transducer corresponding to several distances,
    iterating the choosing step and the calculating step for several assumed values of the speed of sound to be measured, and
    determining the global speed of sound by applying an optimization criteria to the correlation coefficients obtained for each assumed value for the speed of sound to be measured.

2. The method according to claim 1, wherein the organ is the liver.

3. The method according to claim 1, wherein the ultrasound probe comprises less than 5 circles.

4. The method according to claim 1, wherein the additional portions of circles are symmetrical.

5. The method according to claim 1, wherein an operating wavelength is defined for the ultrasound probe, a space between two circles being inferior or equal to five times the operating wavelength.

6. The method according to claim 1, wherein the ultrasound probe comprises a set of transducer elements and the number of transducer elements ranges from 3 to 64.

7. The method according to claim 1, wherein the optimization criteria maximizes at least one of an autocorrelation function and a coherence factor, the coherence factor being proportional to a ratio of coherent ultrasound energy received by the ultrasound probe and incoherent ultrasound energy received by the ultrasound probe.

8. The method according to claim 1, wherein the method comprises carrying out one of the following calculation techniques:
    a first calculation technique in which:
        a spatial coherence function corresponding to evolution of a value of the correlation coefficients with distance for each backscattered echo is established, and
        a statistical estimator is applied to the spatial coherence function to obtain a mean spatial coherence function, and
    a second calculation technique in which:
        a statistical estimator is applied to the correlation coefficients calculated at the same distance for several received backscattered echoes to obtain mean correlation coefficients.

9. The method according to claim 1, wherein the organ comprises a tissue structure with depth, wherein sound propagation in the tissue structure with depth is modeled by a layered model comprising several layers with depth, the method for measuring further comprising deducing several local speeds of sound in a region of interest from several global speeds of sound by using the layered model, the global speeds of sound being measured for respective depths, said depths comprising at least one depth per layer of the layered model.

10. The method according to claim 1, wherein the method comprises at least one of the following steps:
    predicting that the subject is at risk of suffering from an obesity related disease based on the at least one parameter measured, and
    diagnosing the obesity related disease based on the at least one parameter measured.

11. A computer program product comprising program instructions, the computer program instructions being loadable into a data-processing unit and adapted to cause execution of at least one step of the method according to claim 1 when run by the data-processing unit.

12. A non-transitory computer readable medium having encoded thereon computer program instructions which, when executed by a data-processing unit, cause execution at least one step of the method according to claim 1.

13. A device for measuring at least one parameter of a region of interest of an organ of a subject, one parameter being a global speed of sound in the region of interest, the global speed of sound in the region of interest being determined by integrating a speed of sound at several depths of the region of interest, the speed of sound at a given depth being named a local speed of sound, the device comprising:
    an ultrasound probe comprising a set of elements of transducer, at least some of the elements of transducer being arranged along circles, wherein the set of elements of transducer are arranged according to a spatial arrangement in which some elements of the transducers are arranged along concentric circles and other elements of the transducer are arranged along additional portions of circle, the additional portions of circle extending between two extremities, each extremity belonging to a largest of the concentric circles, the ultrasound probe being adapted to:

apply several ultrasound pulses, and obtain over time several backscattered echoes from the region of interest corresponding to several excitations of the region of interest by ultrasound pulses applied with the ultrasound probe, a unit for controlling the relative movement of the ultrasound probe and the region of interest between each excitation, and a calculator adapted for:

choosing an assumed value for a speed of sound to be measured, calculating correlation coefficients of at least one backscattered echoes by using the assumed value, a correlation coefficient being equal to a correlation between an echo signal backscattered by a region of a the tissue and received by a first element of transducer and an echo signal backscattered by the same region of the tissue and received by a second element of transducer positioned at a given distance from the first element of transducer, the correlation coefficients being calculated for several pairs of elements of transducer corresponding to several distances, iterating the choosing step and the calculating step for several assumed values for the speed of sound to be measured, and determining the global speed of sound based on applying an optimization criteria to the correlation coefficients obtained for each assumed value for the speed of sound to be measured.

14. The device of claim 13, further comprising a sensor adapted to measure at least another physical value which is chosen from the group consisting of a value representative of stiffness, a value representative of deformation, shear viscosity, contractility, a degree of anisotropy of fibers comprised in the region of interest and a direction of the fibers comprised in the region of interest, each measured physical value being a parameter of the region of interest.

* * * * *